US006056705A

United States Patent [19]

Stigar-Brown

[11] Patent Number: 6,056,705

[45] Date of Patent: May 2, 2000

[54] CLITORAL CLIP

[76] Inventor: Kathleen R Stigar-Brown, 9856 Costa Mesa La.#610, Bonita Springs, Fla. 34135

[21] Appl. No.: 09/119,248

[22] Filed: Jul. 20, 1998

[51] Int. Cl.[7] .................... A61M 7/00

[52] U.S. Cl. .................... 601/84; 601/46; 601/89; 601/133

[58] Field of Search .................... 601/46, 67, 68, 601/69, 70, 72, 80, 84, 89, 133; 29/208, DIG. 46; 433/159, 4, 160; 140/106, 121; 606/205–211, 133; 81/416, 319, 321, 322, 323, 324, 328; 482/49

[56] References Cited

U.S. PATENT DOCUMENTS

| | | | |
|---|---|---|---|
| 632,843 | 9/1899 | McGhee | 433/159 |
| 2,698,483 | 1/1955 | Berkowitz | 433/159 |
| 4,538,485 | 9/1985 | Saila | 81/336 |
| 5,243,997 | 9/1993 | Uflacker et al. | 604/22 |
| 5,484,447 | 1/1996 | Waldock et al. | 606/107 |
| 5,542,843 | 8/1996 | Price | 433/159 |

FOREIGN PATENT DOCUMENTS

| | | | |
|---|---|---|---|
| 2316911 | 2/1977 | France | 433/159 |
| 1466733 | 3/1989 | U.S.S.R. | 433/159 |

*Primary Examiner*—Richard J. Apley
*Assistant Examiner*—Justine R. Yu
*Attorney, Agent, or Firm*—Michael I. Kroll

[57] ABSTRACT

A clitoral stimulation clip for providing a vibratory sensation to an erogenous zone of a user to increase sexual stimulation. The clitoral stimulation clip includes a first member having a first gripping portion and a first clamping portion and a second member having a second gripping portion and a second clamping portion pivotally connected to the first member to form a clamping section therebetween. A clamping device releasably secures the first and second members in a clamped position and a vibrating device causes the clitoral stimulation clip to vibrate. The clitoral stimulation clip is movable between a first position in which the first and second gripping portions are moved together causing the first and second clamping portions to be separated whereby the erogenous zone of the user may be received within the clamping section between the first and second clamping portions and a second position in which the first and second gripping portions are separated causing the first and second clamping portions to move towards each other whereby the erogenous zone is retained within the clamping section by engaging the clamping device to clamp the first and second members in a stationary position and the vibrating device is activated to vibrate thereby stimulating the erogenous zone.

9 Claims, 2 Drawing Sheets

Fig. 3
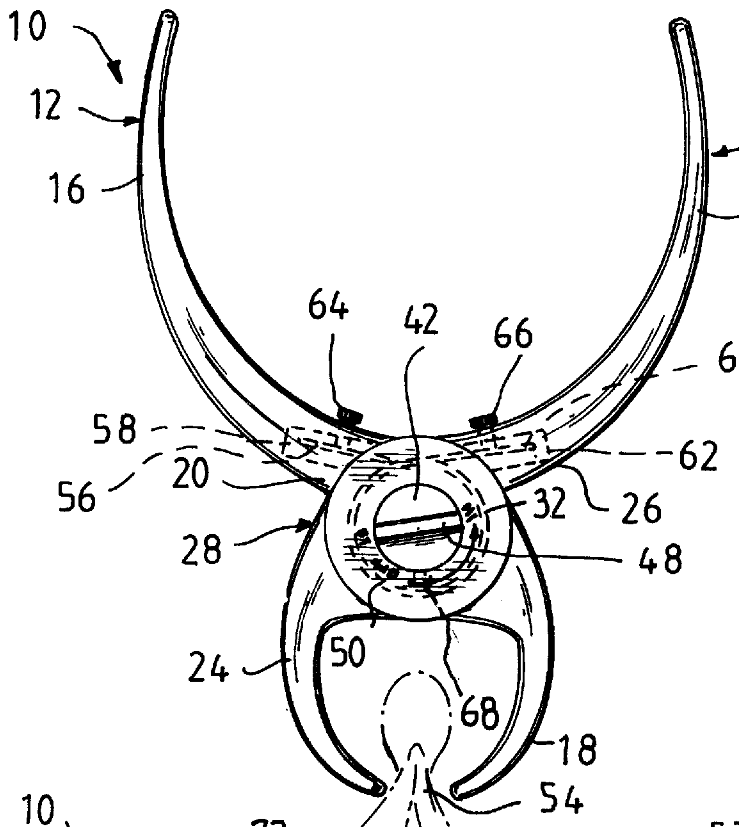
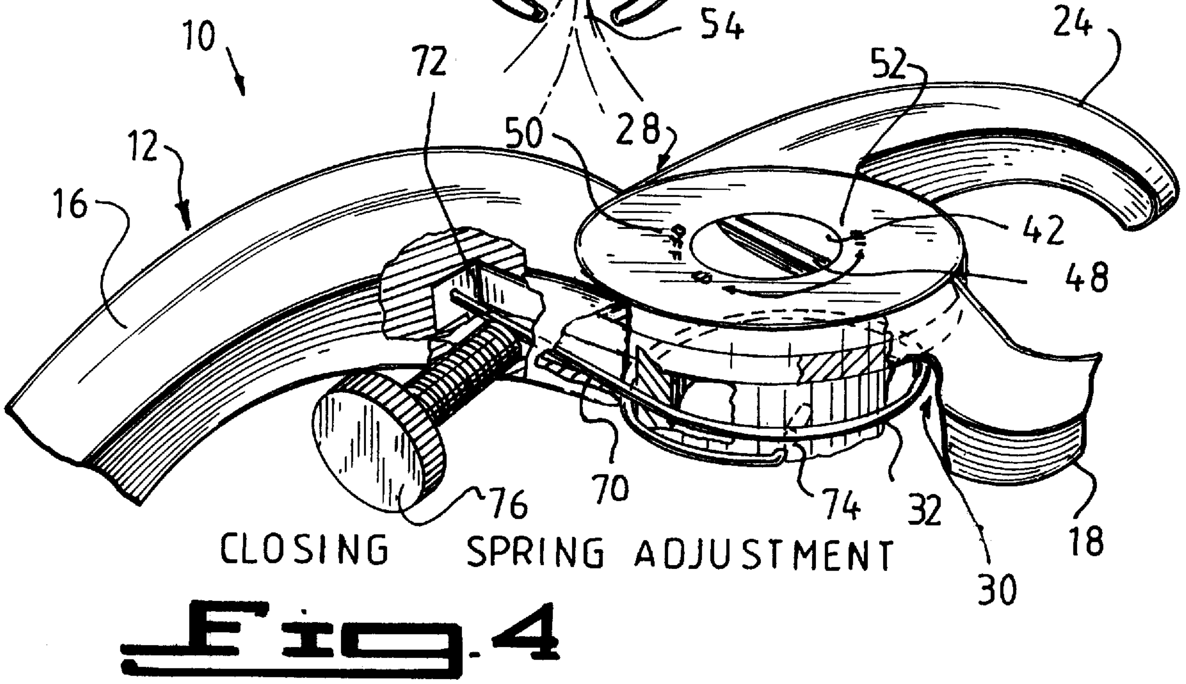
Fig. 4

CLITORAL CLIP

BACKGROUND OF THE INVENTION

1. Field of the Invention

The present invention relates generally to devices for providing sexual stimulation and, more specifically, to a vibrating clip removably connected to the external genetalia of a woman for enhancing sexual activity and providing sexual stimulation.

2. Description of the Prior Art

Numerous devices for providing sexual stimulation have been provided in the prior art. For example, U.S. Pat. Nos. 4,790,296; 5,067,480; 5,460,597 and 5,470,303 all are illustrative of such prior art. While these units may be suitable for the particular purpose to which they address, they would not be as suitable for the purposes of the present invention as heretofore described.

U.S. Pat. No. 4,790,296

Inventor: Daniel A. Siegal

Issued: Dec. 13, 1988

An apparatus for engaging the glans of a user to provide sexual stimulation includes an electric motor situated within a box-like, sound insulated container, an elongated arm extending through a container aperture and having a first end coupled to a drive shaft turned by the motor, and a glans engaging attachment fixed to a second end of the elongated arm. A drive wheel having a plurality of apertures therethrough is attached to the drive shaft, and an intermediate arm is pivotally attached at one end to the elongated arm and at the other r end to the drive wheel. This has the effect of translating the rotational motion of the drive shaft into reciprocating and substantially linear motion of the elongated arm along its longitudinal axis. In one preferred form, the glans engaging attachment comprises a dildo member having a projecting shaft held securely adjacent the second end of the elongated arm. In another preferred form, the glans engaging attachment includes a rigid bell having an outwardly projecting tubular shaft held securely adjacent the second end of the elongated arm, and a soft tubular sleeve placed onto the bell in a manner forming a receptacle for the glans penis.

U.S. Pat. No. 5,067,480

Inventor: Philippe-Guy E. Woog et al.

Issued: Nov. 26, 1991

A stimulator for use in marital orgasmic therapy is provided. The stimulator uses a step-down transformer and a water-proof case. The stimulator oscillates at 2000–8000 (preferably 3000–3600) cycles per minute throughout an angle of operation chosen from the range of 10 to 80 (preferably 20 to 60) degrees. An integrated set includes several different detachable attachments and a handle with mechanical oscillating means.

U.S. Pat. No. 5,460,597

Inventor: George Hopper

Issued: Oct. 24, 1995

A stimulator for use in marital orgasmic and sexual therapy for performing a simulation of cunnilingus is provided. The stimulator has an elongated cylindrical housing, simulated lips, a simulated tongue and is battery powered. The tongue is caused to move in and out with respect to the simulated lips; up and down; and side to side. These motions are attainable independently of the others. Three motors, separate switches, and three sets of cooperating but independent linkage are provided to accomplish this motion arrangement. A finger operated plunger type dispenser integral to the housing dispenses lubricant, medication, or other fluid onto the simulated tongue.

U.S. Pat. No. 5,470,303

Inventor: Cynthia D. Leonard et al.

Issued: Nov. 28, 1995

Conventional massage devices of the sexual self-stimulator type include reciprocating massage beads. Some devices of this type feature rotary massage beads. A novel device includes a housing containing a drive and carrying a soft, flexible, resilient, tongue-shaped head on one end thereof, the head containing an arcuate shaft with a straight inner end connected to the drive, whereby the path of travel of the shaft during rotation defines an ellipsoid with a cone on the outer free end thereof.

SUMMARY OF THE PRESENT INVENTION

The present invention relates generally to devices for providing sexual stimulation and, more specifically, to a vibrating clip removably connected to the external genetalia of a woman for enhancing sexual activity and providing sexual stimulation.

A primary object of the present invention is to provide a clitoral stimulation clip that will overcome the shortcomings of prior art devices.

Another object of the present invention is to provide a clitoral stimulation clip which is able to provide mechanical stimulation to the external genitalia of a female.

An additional object of the present invention is to provide a clitoral stimulation clip which is able to assist a woman incurring difficulties in achieving orgasms.

A further object of the present invention is to provide a clitoral stimulation clip able to supplement and enhance sexual activity.

A yet further object of the present invention is to provide a clitoral stimulation clip including a spring action clip which acts to surround the clitoris of a woman while vibrating to assist the woman in achieving an orgasm.

A still further object of the present invention is to provide a clitoral stimulation clip which is able to be positioned to grasp the external genitalia of a woman and operate in a “hands free” manner.

An even further object of the present invention is to provide a clitoral stimulation clip which is made of a material which will not react adversely with the skin of the user.

Another object of the present invention is to provide a clitoral stimulation clip that is simple and easy to use.

A still further object of the present invention is to provide a clitoral stimulation clip that is economical in cost to manufacture.

Additional objects of the present invention will appear as the description proceeds.

A clitoral stimulation clip for providing a vibratory sensation to an erogenous zone of a user to increase sexual stimulation. The clitoral stimulation clip includes a first member having a first gripping portion and a first clamping portion and a second member having a second gripping portion and a second clamping portion pivotally connected to the first member to form a clamping section therebetween. A clamping device releasably secures the first and second members in a clamped position and a vibrating device causes the clitoral stimulation clip to vibrate. The clitoral stimulation clip is movable between a first position in which the first and second gripping portions are moved together causing the first and second clamping portions to be separated whereby the erogenous zone of the user may be received within the clamping section between the first and second clamping portions and a second position in which the first and second gripping portions are separated causing the first and second clamping portions to move towards each other whereby the erogenous zone is retained within the clamping section by engaging the clamping device to clamp the first and second members in a stationary position and the vibrating device is activated to vibrate thereby stimulating the erogenous zone.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

FIG. 3 is a top perspective view of the clitoral stimulation clip of the present invention clamping a clitoris between its clips; and FIG. 4 is perspective partial cross-sectional view with parts cut away illustrating the spring adjustment feature of the clitoral stimulation clip of the present invention.

DESCRIPTION OF THE REFERENCED NUMERALS

Figure 1:
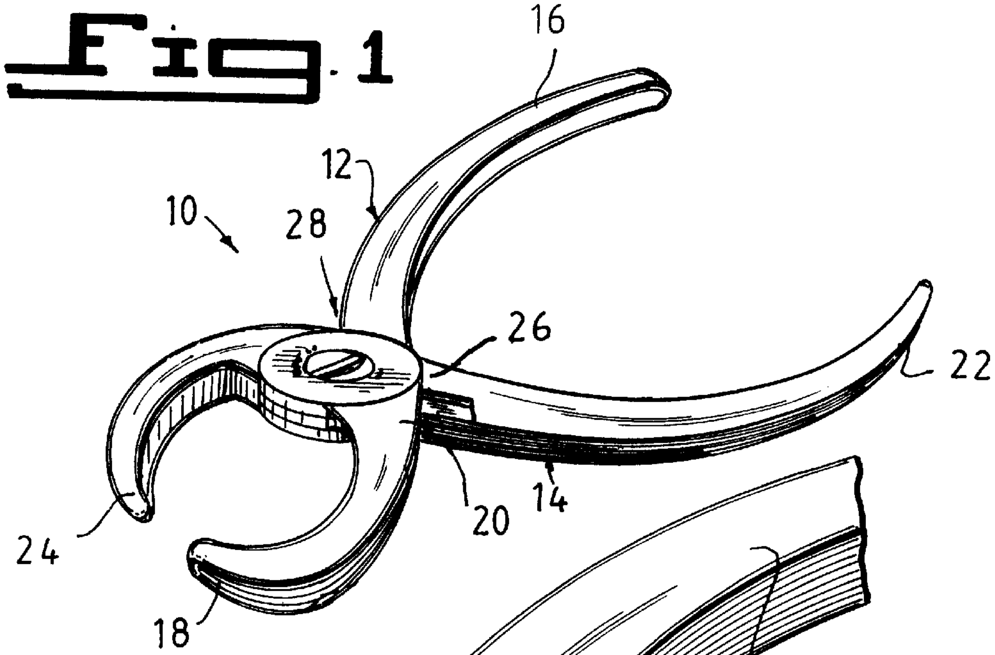
FIG. 1 is a top perspective view of the clitoral stimulation clip in accordance with the present invention in the closed position, the open position is illustrated in dashed lines.

Turning now descriptively to the drawings, in which similar reference characters denote similar elements throughout the several views, the Figures illustrate the clitoral stimulation clip of the present invention. With regard to the reference numerals used, the following numbering is used throughout the various drawing figures.

10 clitoral stimulation clip of the present invention
12 first member
14 second member
16 grip portion of first member
18 clamp portion of first member
20 connection point of first member
22 grip portion of second member
24 clamp portion of second member
26 connection point of second member
28 pivotal connection between first and second members
30 gap for housing spring
32 clamping spring
34 recess between connection points of first and second members
36 vibrator motor
38 vibrator adjustment spring
40 power source
42 cap
44 thread spiraling around base of cap
46 thread spiraling around inside of recess
48 knob on top of cap
50 vibrator motor "OFF" indicia
52 vibrating speed indicia
54 clitoris of user
56 first leg of clamping spring
58 recess within first member for receiving first leg of clamping spring
60 second leg of clamping spring
62 recess within second member for receiving second leg of clamping spring
64 first clamping screw
66 second clamping screw
68 connection between spring and cap
70 first end of clamping spring
72 recess for receiving first end of clamping spring
74 second end of clamping spring connecting clamping spring to cap
76 clamping screw

DETAILED DESCRIPTION OF THE PREFERRED EMBODIMENT

Turning now descriptively to the drawings, in which similar reference characters denote similar elements throughout the several views, FIGS. 1–4 illustrate the clitoral stimulation clip of the present invention, indicated generally by the numeral 10.

The clitoral stimulation clip 10 of the present invention is illustrated in FIGS. 1–4. The clitoral stimulation clip 10 includes a first member 12 pivotally connected to a second member 14. The first member 12 includes a grip portion 16 and a clamp portion 18 with a connection point 20 formed therebetween. The second member 14 also includes a grip portion 22 and a clamp portion 24 with a connection point 26 formed therebetween. The first and second members 12 and 14 are positioned to cross each other at the connection points 20 and 26 forming a pivotal connection 28 therebetween.

Movement of the first and second members 12 and 14 with respect to each other is illustrated in FIG. 1. As can be seen from this figure, during a gripping operation, as the grip portions 16 and 22 are moved further apart, the clamp portions 18 and 24 are caused to move further apart. The first and second members 12 and 14 can be held at any desired clamping distance from one another due to a locking mechanism which will be described in greater detail hereinafter with specific reference to FIGS. 3 and 4. As is also illustrated in FIG. 1, during a releasing operation the grip portions 16 and 22 of the first and second members 12 and 14 are gripped by a user and caused to move towards each other causing the clamping portions 18 and 24 of the first and second members 12 and 14 to move together.

Figure 2:
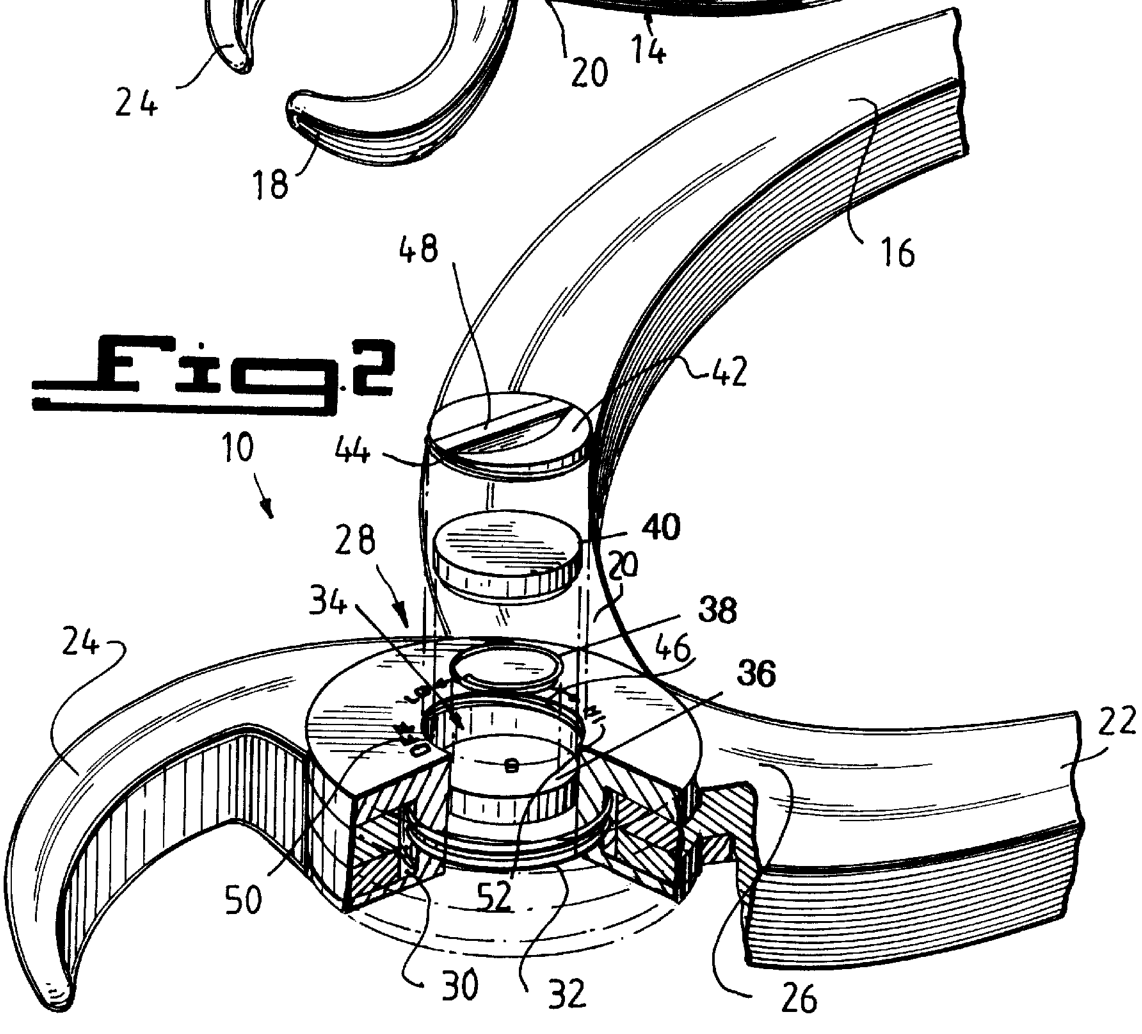
FIG. 2 is a front perspective partial cross-sectional view of the clitoral stimulation clip of the present invention illustrating the electronic components thereof in expanded form.

An exploded partial cross-sectional view of the pivotal connection is illustrated in FIG. 2. As can be seen from this figure, the first and second members 12 and 14 form an interlocking relationship with one another. The preferred interlocking relationship between the first and second members 12 and 14 is similar to the connection between the elements of a conventional pair of pliers. Between the first and second members 12 and 14 at the pivotal connection 28 is a gap 30. The gap 30 is used for housing a clamping spring 32 for holding the first and second members 12 and 14 of the clitoral stimulation clip 10 at a desired spatial or clamping distance when held in a stressed position. The spring 32 also acts to return the first and second members 12 and 14 to an at rest position when allowed to uncoil. A recess 34 is also formed between the connection points 20 and 28 of the first and second members 12 and 14. The recess 34 is separated from the gap 30 housing the spring 32 therein. Positioned within the recess 34 is a vibrator motor 36. The vibrating motor 36 includes a vibrator adjustment spring 38 for controlling the speed of vibration of the vibrating motor 36. A power source 40 is also connected to supply power to the vibrating motor 36 causing it to vibrate. Although the power source 40 illustrated is a battery, any known source of voltage may be adapted to provide power to the vibrator motor 36. Located above the power source 40 and closing the recess 34 to the atmosphere is a cap 42. The cap 42 includes a thread 44 spiraling therearound which mates with a thread 46 spiraling around the inside of the recess 34 and acts to control the application of power from the power source 40 to the vibrating motor 36 and the speed of vibration. The cap 42 includes a knob 44 to be turned by the user, causing the cap 42 to ride along the thread 46 and be forced further into the recess 34. The cap 42 is initially turned so that the knob 48 thereon points to the indicia labeled “OFF”. In this position, the power source 40 is separated or disconnected from the vibrator motor 36 and the clitoral stimulation clip 10 does not vibrate. As the knob 48 is turned, the cap 42 is forced further down into the recess 34 pushing the power source 40 towards and into contact with the vibrator motor 36. When the power source 40 contacts the vibrator motor 36 it causes the vibrator motor 36 to turn on and the clitoral stimulation clip 10 to vibrate. The cap 42 is also connected to the vibrator adjustment spring 38 whereby as the knob 48 is turned the vibrator adjustment spring 38 is tightened, i.e. tensioned, and the vibrator motor 36 is caused to vibrate faster. The speed at which the vibrator motor 36 will vibrate is indicated by the indicia 52 printed around the cap 42. When the knob 48 is turned in the opposing direction the vibrator adjustment spring 38 is caused to uncoil whereby the vibrator motor 36 is caused to rotate more slowly until the knob 48 points to the indicia labeled off 50. In this position the connection between the power source 40 and the vibrator motor 36 is removed.

While a preferred mechanism for producing a vibratory motion causing the clitoral stimulation clip 10 to vibrate is shown and described herein, those of ordinary skill in the art who have read this description will appreciate that there are numerous other mechanisms for producing a vibratory motion causing the clitoral stimulation clip 10 to vibrate, e.g. an oscillator, and, therefore, as used herein the phrase “vibrating means for imparting vibratory motion” should be construed as including all such mechanisms as long as they achieve the desired result of producing a vibratory motion causing the clitoral stimulation clip 10 to vibrate, and, therefore, that all such alternative mechanisms are to be considered as equivalents to the one described herein.

FIG. 3 illustrates the clitoral stimulation clip 10 of the present invention positioned to surround the clitoris 54 of a user. The mechanism for retaining the clitoral stimulation clip 10 in a locked position is illustrated in dashed lines. The clamping spring 32 is illustrated within the recess 30 and includes a first end 56 extending into a recess 58 within the first member 12 and a second end 60 extending into a recess 62 within the second member 14. A first clamping screw 64 extends into the first member 12 and the recess 58 to engage the first end 56 of the clamping spring 32. A second clamping screw 66 extends into the second member 14 and recess 62 to engage the second end 60 of the clamping spring 32. An extension leg 68 extends from the clamping spring 32 and engages one of the first and second members 12 or 14 for securing the clamping spring 32 in position. When a user grasps the grip portions 16 and 22 of the clitoral stimulation clip 10 so as to separate them, the clamp members 18 and 24 are caused to move closer to each other. When the clitoral stimulation clip 10 is positioned so that the clitoris 54 of the user is positioned between the clamping portions 18 and 24 and the clamp members 18 and 24 are caused to move closer to each other, the clitoris 54 is caused to be clamped between the clamping portions 18 and 24. The user will then turn the first and second clamping screws 64 and 66 causing them to engage the first and second ends 56 and 60, respectively, of the clamping spring 32, preventing the clamping spring 32 from uncoiling. When the clamping spring 32 is prevented from uncoiling, the clamp portions 18 and 24 are clamped in position with the clitoris 54 of the user held therebetween. The clitoral stimulation clip 10 is now in position and ready for use. In order to release the clitoral stimulation clip 10, the clamping screws 64 and 66 must be turned in the opposite direction to release the engagement with the first and second ends 56 and 60, respectively, of the clamping spring 32 thereby allowing the clamping spring 32 to recoil. This allows the first and second clamp sections 18 and 24 and thus the first and second grip portions 16 and 22 to return to their rest position.

An alternative embodiment of the clamping mechanism is illustrated in FIG. 4. In this embodiment, a first end 70 of the clamping spring 32 is received by a recess 72 extending through one of the first and second members 12 and 14. The second end 74 of the clamping spring 32 is securely engaged with the other of the first and second members 12 and 14. A clamping screw 76 extends into the one of the first and second members 12 and 14 in which the clamping spring 32 extends so as to engage the clamping spring 32 and hold the clitoral stimulation clip 10 in a locked position. When a user grasps the grip portions 16 and 22 of the clitoral stimulation clip 10 so as to separate them, the clamp members 18 and 24 are caused to move closer to each other. When the clitoral stimulation clip 10 is positioned so that the clitoris 54 of the user is between the clamping portions 18 and 24 and the clamp members 18 and 24 are caused to move closer to each other, the clitoris 54 is caused to be clamped between the clamping portions 18 and 24. The user will then turn the clamping screw 76 causing it to engage the first end 70 of the clamping spring 32, preventing the clamping spring 32 from uncoiling. The second end 74 of the clamping screw 32 is secured to the other of the first and second members 12 and 14 and thereby secured in place. When the clamping spring 32 is prevented from uncoiling, the clamp portions 18 and 24 are clamped in position with the clitoris 54 of the user held therebetween. The clitoral stimulation clip 10 is now in position and ready for use. In order to release the clitoral stimulation clip 10, the clamping screw 76 must be turned in the opposite direction to release the engagement with the first end 70 of the clamping spring 32 thereby allowing the clamping spring 32 to recoil. This allows the first and second clamp sections 18 and 24 and thus the first and second grip portions 16 and 22 to return to their rest position.

While a preferred mechanism for clamping the clitoral stimulation clip 10 in a locked clamping position is shown and described herein, those of ordinary skill in the art who have read this description will appreciate that there are numerous other mechanisms for clamping the clitoral stimulation clip 10 in a locked clamping position and, therefore, as used herein the phrase "means for clamping the clitoral stimulation clip in a locked clamping position" should be construed as including all such mechanisms as long as they achieve the desired result of clamping the clitoral stimulation clip 10 in a locked clamping position, and, therefore, that all such alternative mechanisms are to be considered as equivalents to the one described herein.

The operation of the clitoral stimulation clip 10 of the present invention will now be described with reference to the figures and specifically FIGS. 2 and 3. In operation, the clitoral stimulation clip 10 is grasped by a user at the grip portions 16 and 22. The user then squeezes the grip portions 16 and 22 together causing the clamp portions 18 and 24 to move apart. The clamp portions 18 and 24 are now positioned to surround the clitoris 54 of the user. The user now grasps the grip portions 16 and 22 so as to separate them. This causes the clamp portions 18 and 24 to move towards each other clamping the clitoris 54 of the user therebetween.

The first and second clamping screws 64 and 66 are now turned to extend further into their respective one of the first and second members 12 and 14. As the clamping screws 64 and 66 are turned they are caused to extend into the recesses 58 and 62 and contact the first and second ends 56 and 60, respectively, of the clamping spring 32. The engagement between the first and second clamping screws 64 and 66 and the first and second ends 56 and 60, respectively, of the clamping spring 32 prevents the clamping spring 32 from uncoiling and holds the clitoral stimulation clamp 10 in a clamped position retaining the clitoris 54 of the user between the clamp portions 18 and 24.

At this point the user will grasp and turn the knob 48 of the cap 42. Turning the knob 48 causes the cap 42 to ride down along the thread 46 within the recess 34 further down into the recess 34. The cap 42 contacts the power source 40 causing it to move further into the recess 34 until it contacts the vibrator motor 36. At this point the vibrator motor 36 is caused to turn on, vibrating the clitoral stimulation clip 10. As the knob 48 is turned further the vibrator adjustment spring 38 is caused to coil causing the vibrator motor 36 to vibrate faster. The knob 48 is turned until the clitoral stimulation clip 10 is vibrating at the desired speed. The user now begins sexual activity.

Once the user is completed with the sexual activity, the knob 48 is turned in the opposite direction. This allows the vibrator adjustment spring 38 to uncoil and the power source 40 to rise up in the recess 34 breaking the contact with the vibrator motor 36. The knob 48 is turned until it points to the "OFF" indicia 50 printed on the clitoral stimulation clip 10. At this point, the user will turn the first and second clamping screws 64 and 66 releasing the engagement with the first and second ends 56 and 60 of the clamping spring 32. The clitoral stimulation clip 10 is now released from its locked position and can be removed from its position surrounding the clitoris 54 of the user.

The clitoral stimulation clip 10 may be formed of any type of material which will perform the above described functionsand will not react adversely with the skin of a user such as to caause chafing, rashes or any other reaction.

From the above description it can be seen that the clitoral stimulation clip of the present invention is able to overcome the shortcomings of prior art devices by providing a clitoral stimulation clip which is able to provide mechanical stimulation to the external genitalia of a female to supplement and enhance sexual activity and to assist a woman incurring difficulties in achieving orgasms. The clitoral stimulation clip includes a spring action clip which surrounds the clitoris of a woman while vibrating to assist the woman in achieving an orgasm. The clitoral stimulation clip is also able to be positioned to grasp the external genitalia of a woman and operate in a "hands free" manner while being made of a material which will not react adversely with the skin of the user. Furthermore, the clitoral stimulation clip of the present invention is simple and easy to use and economical in cost to manufacture.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A clitoral stimulation clip for providing a vibratory sensation to an erogenous zone of a user to increase sexual stimulation, said clitoral stimulation clip comprising:

a) a first member including a first gripping portion and a first clamping portion;

b) a second member crossing said first member including a second gripping portion and a second clamping portion, a pivotal connection between said members where said members cross each other to form a clamping section between the clamping portions of said members;

c) means mounted in said pivotal connection for releasably securing said first and second members in a clamped position; and d) means mounted in said pivotal connection for vibrating said clitoral stimulation clip to stimulate the erogenous zone when said members are in the clamped position.

2. The clitoral stimulation clip as recited in claim 1, further comprising a recess extending into said first and second members for retaining said vibrating means therein.

3. The clitoral stimulation clip as recited in claim 2, wherein said vibrating means includes a vibrator motor and a power source selectively connected to said vibrating motor.

4. The clitoral stimulation clip as recited in claim 3, wherein said vibrating means further includes an adjustment spring coupled to adjust a vibration speed of said vibrating motor.

5. The clitoral stimulation clip as recited in claim 4, further comprising a rotatable cap for sealing said recess.

6. The clitoral stimulation clip as recited in claim 5, wherein said power source is positioned between said cap and said vibrator motor wherein turning of said cap in a first direction causes said cap to ride along said thread within said recess and into said recess causing said power source to move further into said recess and contact said vibrating motor thereby activating said vibrating motor.

7. The clitoral stimulation clip as recited in claim 6, wherein said adjustment spring is connected to said cap wherein, when said cap is rotated in said first direction tension is induced in said adjustment spring causing said vibrating motor to vibrate at a faster rate.

8. The clitoral stimulation clip as recited in claim 6, wherein said cap further includes a knob for use in turning by the user.

9. The clitoral stimulation clip as recited in claim 7, further comprising indicia positioned about said recess indicating a vibration speed of said vibrating motor, said knob including means for pointing to said indicia to indicate the present vibrational speed of said vibrating motor.

* * * * *